United States Patent [19]
Weissenfluh et al.

[11] Patent Number: 5,562,275
[45] Date of Patent: Oct. 8, 1996

[54] RADIALLY AND LONGITUDINALLY INDEFORMABLE FLEXIBLE SPINDLE

[75] Inventors: Hans v. Weissenfluh, Magadino; Beat A. v. Weissenfluh, Gentilino, both of Switzerland

[73] Assignee: Hawe Neos Dental Dr. H. v. Weissenfluh AG, Bioggio, Switzerland

[21] Appl. No.: 501,173

[22] Filed: Jul. 11, 1995

[30] Foreign Application Priority Data

Jul. 11, 1994 [CH] Switzerland ............ 02 203/94

[51] Int. Cl.⁶ .............. A61B 5/00; A61C 1/18; A61C 5/12
[52] U.S. Cl. .......... 267/155; 267/168; 128/772; 433/39; 464/58
[58] Field of Search ................ 267/154, 157, 267/168; 128/772, 778; 433/39; 604/264; 464/58

[56] References Cited

U.S. PATENT DOCUMENTS

| | | |
|---|---|---|
| 3,435,905 | 4/1969 | Lazarus et al. |
| 3,852,884 | 12/1974 | Lazarus ............... 433/39 |
| 5,052,404 | 10/1991 | Hodgson ............... 267/168 |
| 5,165,421 | 11/1992 | Fleischhacker et al. ...... 267/168 |
| 5,211,636 | 5/1993 | Mische ............... 128/772 |

FOREIGN PATENT DOCUMENTS

| | | |
|---|---|---|
| 4208221 | 9/1993 | Germany. |
| WO9409716 | 5/1994 | WIPO. |

*Primary Examiner*—Robert J. Oberleitner
*Assistant Examiner*—Chris Schwartz
*Attorney, Agent, or Firm*—Marks & Murase L.L.P.

[57] ABSTRACT

A flexible spindle suitable for transmitting a torque as well as an axial thrust is constituted by a plurality of helical spirals of wire all of the same length. Each spiral has opposite winding directions to the winding direction of the adjacent spirals and the outer diameter of each spiral is equal to the inner diameter of the spiral which surrounds it. The terminal ends of the spirals are assembled integrally with each other and with the terminal ends of a flexible member situated inside the innermost spiral. Each sprial has a length which is equal to that of the other spirals as measured along their axis when these are in their bent operating position and under those conditions under which they are designed to transmit torque and thrust, with the flexible spindle resulting not to be radially or longitudinally deformable when under stress, thus transmitting the forces without loss.

2 Claims, 3 Drawing Sheets

RADIALLY AND LONGITUDINALLY INDEFORMABLE FLEXIBLE SPINDLE

The present invention relates to field of flexible spindles for transmitting a torque which simultaneously resist to forces while applying an axial pull or a compression.

BACKGROUND OF THE INVENTION

The problem which the present invention addresses relates to a flexible spindle which is suitable for transmitting a torque without undergoing any deformations in radial or longitudinal direction owing to the effect of the stresses deriving from the simultaneous application of said torque and an axial pull or compression force to it.

At present flexible sheaths exist like, e.g., the one which is disclosed in the German Patent Publication No. 4,208,221, which is used as catheter for transmitting relatively low radial and axial forces. This document further discloses spirals of different length, whereby less spirals are used in order to facilitate sharp bending of the catheter. The flexible spindle consists of coaxial helical spirals each having a winding direction opposite to the winding direction of the adjacent spiral.

U.S. Pat. No. 3,435,905 discloses further an angle drive tool for transmitting a torque but no axial forces. The flexible sleeve consists of a pair of helical springs which are coaxially telescoped and oppositely wound.

Starting from this prior art it is the object of the present invention to provide for a flexible spindle which is capable of transmitting both radial and axial forces without deformation of the spindle, with small loss of the force applied.

SUMMARY OF THE INVENTION

This object is attained with a flexible spindle suitable for transmitting a torque as well as an axial force, said flexible spindle being constituted by at least two coaxial helical spirals having the same axial length, with each spiral having its winding direction opposite to the winding direction of the adjacent spiral(s) and the outer diameter of each spiral being equal to the inner diameter of that spiral which surrounds it, with the terminal ends of said spirals assembled together with each other and with the terminal ends of a non-extensible flexible element situated inside the interior of the hollow defined by the smallest-diameter spiral and having a longitudinal development which is equal to the longitudinal development of the spirals as measured along their axis when the same spirals are positioned in their bent operating position and under the conditions under which they are designed to transmit said torque, with the flexible spindle thus resulting being radially and longitudinally indeformable during the transmission of a torque having a prefixed revolution direction and/or an axially directed force.

The solution of the above said problem makes it possible to use flexible spindles in a large number of technical applications, e.g., in those devices for medical or odontological use which are required to perform with particular accuracy and precision.

The present invention also relates to the use of such a flexible spindle in a tensioning apparatus for matrices for dental use, accomplishing noticeable results in terms of handling and reliability.

BRIEF DESCRIPTION OF THE DRAWINGS

The present invention will be now disclosed in greater detail with reference to the accompanying drawings, wherein.

DETAILED DESCRIPTION OF THE INVENTION

Figure 1:
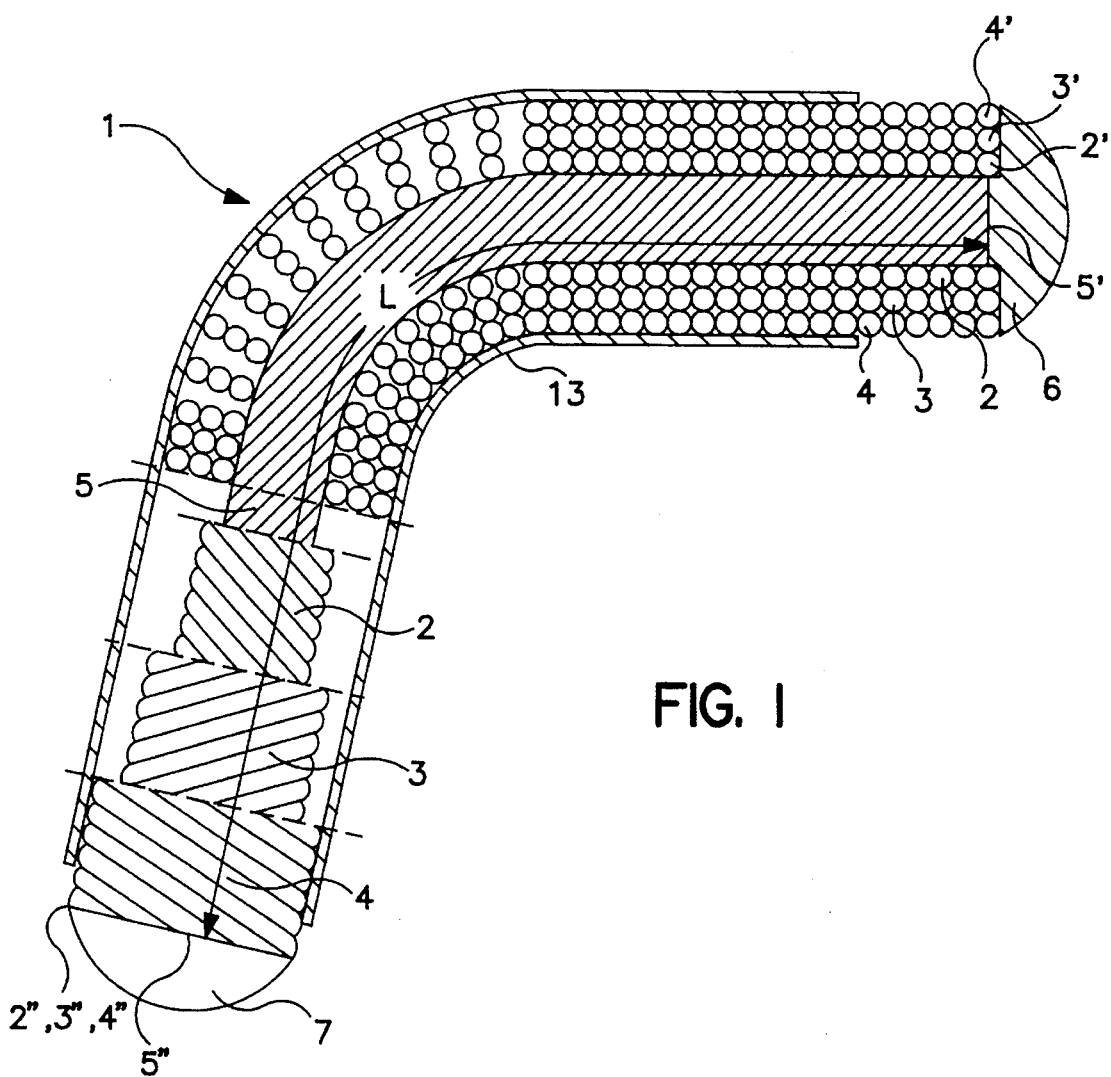
FIG. 1, is an enlarged longitudinal cross-section of a preferred embodiment of the flexible spindle according to the present invention.

As one will see from FIG. 1, three helical spirals 2, 3, 4, made from metal wire and having the same length, are arranged coaxially, whereby the winding direction of spiral 3 is opposite the winding direction of the adjacent spirals 2 and 4. The outer diameter of each of the inner spirals 2, 3 is respectively equal to the inner diameter of the surrounding spirals 3, resp. 4, so that those spirals are always in contact with each other, even when their respective longitudinal axes are deformed when the flexible spindle 1 is bent.

Inside the hollow defined by the innermost spiral 2, i.e., the smallest-diameter spiral from said three spirals, a flexible element 5, preferably made of metal, is inserted which has a length which is equal to the length L of the spirals 2, 3, 4 as measured along their longitudinal axis. The terminal ends 5', 5" of the member 5 are assembled to be integral with the terminal ends of said spirals when said spirals 2, 3, 4 are arranged in their bent operating position and under the conditions under which they are designed to transmit a torque and/or a pull or compression longitudinally.

By applying a torque to an end of such a spindle, which torque is transmitted by said spindle to an organ, according to the direction of application of said torque it would happen, e.g., that both spirals 2 and 4, for a certain direction, would tend to perform a relative rotation of their respective ends 2', 2" and 4', 4", and consequently, with their pitch being modified and their longitudinal length remaining unchanged. This would tend to increase the external diameters of spirals 2 and 4.

But the increase in diameter of spiral 2 is constrained by the spiral 3 which is disposed externally tangent to it.

Inasmuch as the increase in diameter of spiral 2 tends to be impossible, the relative rotation between its terminal ends is consequently prevented as a consequence, the relative rotation between the terminal ends 4' and 4", of the outermost spiral is negligible since it does not undergo any force form the relative movement of the other spirals.

When a torque of opposite direction is applied analogously and symmetrically to the first example, the decrease in diameter of the outermost spiral 4 is prevented by the spiral 3 which, on the contrary, would tend to increase in diameter under such a condition. The mutual counteracting of the spirals 3 and 4 prevents any relative rotation from taking place between their ends 3',3" and 4', 4". Consequently, the spiral 2 does not undergo any torsion from relative movement of the other springs.

It follows from the above that, in whichever way the spirals 2, 3, 4 are inflected, the application of a torque to them does not cause any deformation of the spindle 1 to take place in a radial direction. Thus, their rotation inside a stiff sheath 13, so shaped to cause the flexible spindle 1 to be bent in the desired way, can take place freely, smoothly, or without any stresses caused by frictions between the spirals and the sheath.

The already mentioned flexible member 5 is fixed integrally at its terminal ends 5' and 5" with the ends of the spirals. This element is made from a metal material which is not extensible or compressible by the effect of the stresses it is designed to undergo. As a result of its elasticity, the flexible member 5 prevents any deformations of the spindle 1 in a longitudinal direction which would otherwise occur if only the spirals 2, 3, 4 were present since in the absence of the member 5, the spirals 2, 3, 4 would become deformed as they underwent force exerted in an axial direction.

In order to avoid the risk that even very small plays may arise, resulting in relevant deformations, the flexible member 5 is so dimensioned that, as already briefly mentioned, it is in its normally longitudinally extended situation, with its terminal ends being integral with the ends of the spirals 2, 3, 4. When the spirals 2, 3, 4 are bent in the operating position in which they are required to transmit a torque, flexible member 5 takes a part to a relative extent.

In order to make the ends 5' and 5" of the flexible element 5 integral with the ends of the spirals 2, 3 and 4, which also are preferably made from metal like the flexible member 5, a preferred method of assembly consists in performing two plasma butt-solderings 6, 7 with a material compatible to the materials which constitute the spirals and the flexible member.

If a flexible spindle is required which is non-deformable in longitudinal direction and non-radially deformable due to the effect of a torque only applied according to one prefixed rotation direction, the problem will obviously result to be simplified. By reasoning in analogous terms, it could be thought of a flexible spindle with only two coaxial spirals (this case is not represented in the accompanying figures), wherein the outermost spiral tends to become narrower due to the effect of a relative rotation of its ends, according to the direction of the applied torque, and the innermost tends to expand radially, mutually counteracting as already explained hereinabove.

A practical application of a spindle according to the invention as explained above is for use in the field of dental surgery equipment and disclosed hereinafter.

Such an application relates to a tension matrix and tightening device for odontological use comprising a tensioning gripper, as disclosed in the International Patent Application No. PCT/EP93/02940 by the same Applicant.

Such a device causes the rotary pin of the gripper to rotate and is able to impart an axial pull and an axial pressure on different parts and organs, in order to perform the functions disclosed in the above mentioned publication, and not described in details here.

Until discovery of the present invention, according to the prior art, the apparatus had to be equipped with two separate organs which were required to independently perform the above mentioned rotations or axial shifting application, and the result was a considerable complexity and non-optimal handling characteristics.

Figure 2:
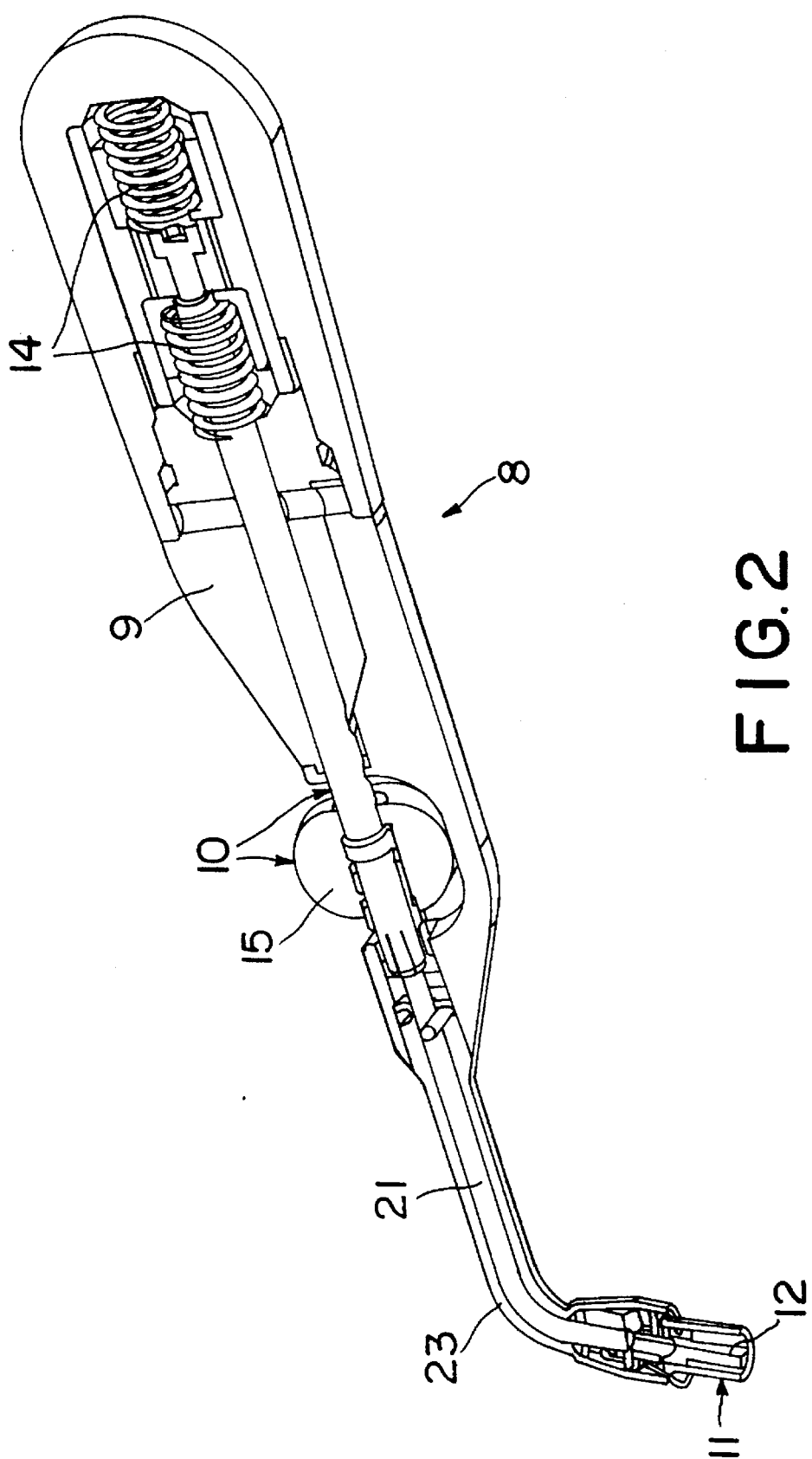
FIG. 2 is a perspective view of a longitudinal section of a tensioning apparatus comprising a matrix tensioning gripper, using a flexible spindle according to the present invention.
Figure 3:
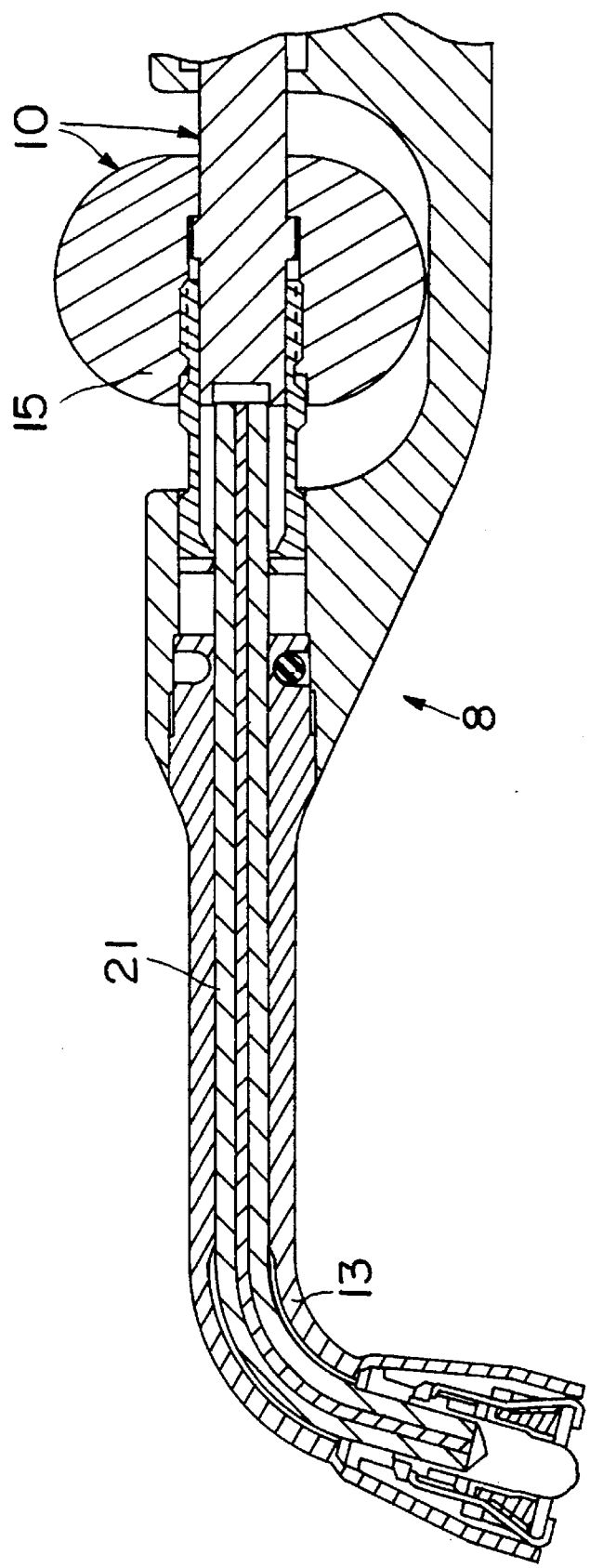
in FIG. 3 is an enlarged longitudinal section of the portion of the apparatus of FIG. 2 with the flexible spindle.

On the contrary, by using a flexible spindle according to the present invention, an apparatus could be provided in which only one actuator organ can perform both function types. See, in this regard, FIGS. 2 and 3.

A tensioning device 8 for actuating a matrix tension gripper 11, besides a handle 9 of known type, an actuator mechanism 10 which, by acting on a knob 15, causes the terminal end of the indeformable flexible spindle 21 of the invention to be axially shifted and/or rotated in order to perform both the coupling, or disengagement, in axial direction, with/from the gripper 11 and the rotation of its rotary pin 12.

This result is essentially due to the indeformability in both radial and longitudinal directions of the flexible spindle 21, which can perform all its functions, even if bent substantially at a right angle inside a stiff sheath 23 coupled with the handle 9, inside which it can slide and rotate under stress without frictions, stickings or movement inaccuracies which would completely impair the functionality of the device owing to the limited size of the matrix tensioning gripper and of the relatively high values of stress.

We claim:

1. A flexible spindle suitable for transmitting a torque as well as an axial force directed along a longitudinal axis of the flexible spindle, said flexible spindle comprising:

a flexible, bendable element having a longitudinal length;

a first helical spiral disposed over said flexible element, said first helical spiral having a first winding direction and a longitudinal length substantially equal to said longitudinal length of said flexible, bendable element; and a second helical spiral disposed coaxially over said first helical spiral, said second helical spiral having a winding direction substantially opposite to the winding direction of said first helical spiral and a length which remains substantially equal to the length of said first helical spiral as the spindle is disposed in a bent position; and at least a third helical spiral disposed coaxially over said second helical spiral, said third helical spiral having a winding direction substantially the same as the winding direction of the first helical spiral and a length which remains substantially equal to the length of said first helical spiral as the spindle is disposed in a bent position;

wherein said first helical spiral, said second helical spiral, said third helical spiral and said flexible element are fastened at respective ends thereof by soldering, said first helical spiral, said second helical spiral, and said third helical spiral transmitting said axial force and transmitting said torque periodically along opposite directions with substantially no radial or longitudinal deformation of the spindle.

2. A tensioning device for odontological use comprising:

(a) a handle;

(b) a flexible spindle comprising:

a flexible, bendable element having a longitudinal length;

a first helical spiral disposed over said flexible element, said first helical spiral having a first winding direction and a longitudinal length substantially equal to said longitudinal length of said flexible, bendable element; and a second helical spiral disposed coaxially over said first helical spiral, said second helical spiral having a winding direction substantially opposite to the winding direction of said first helical spiral and a length which remains substantially equal to the length of said first helical spiral as the spindle is disposed in a bent position; and at least a third helical spiral disposed coaxially over said second helical spiral, said third helical spiral having a winding direction substantially the same as the winding direction of the first helical spiral and a length which remains substantially equal to the length of said first helical spiral as the spindle is disposed in a bent position;

wherein said first helical spiral, said second helical spiral, said third helical spiral and said flexible element are fastened at respective ends thereof by soldering, said first helical spiral, said second helical spiral, and said third helical spiral transmitting an axial force and transmitting torque periodically along opposite directions with substantially no radial or longitudinal deformation of the spindle;

(c) a stiff sheath containing said flexible spindle, said stiff sheath being connected at a first end with said handle and being bent in a prefixed way;

(d) a tensioning gripper disposed at a second end of said stiff sheath;

(e) an actuator mechanism for applying torque at one end of said flexible spindle to effect rotation and axial thrust of said spindle, whereby said actuator mechanism selectively disengages and couples said tensioning gripper; and (f) a spring system suitable for maintaining the actuator mechanism in a prefixed position and for returning the actuator mechanism to a prefixed position when no forces are applied thereto.

* * * * *